United States Patent
Bannigan et al.

(10) Patent No.: US 6,860,984 B2
(45) Date of Patent: Mar. 1, 2005

(54) PH ELECTRODE AND METHODS OF PREPARING AND USING SAME

(75) Inventors: John Thornton Bannigan, Mawson Lakes (AU); Malcolm Rosswyn Haskard, Mawson Lakes (AU); Dennis Estcourt Mulcahy, Mawson Lakes (AU)

(73) Assignee: Gastro Holdings PTY LTD, Mount Lawley (AU)

(*) Notice: Subject to any disclaimer, the term of this patent is extended or adjusted under 35 U.S.C. 154(b) by 368 days.

(21) Appl. No.: 10/005,452

(22) Filed: Nov. 2, 2001

(65) Prior Publication Data

US 2002/0125133 A1 Sep. 12, 2002

Related U.S. Application Data

(63) Continuation-in-part of application No. PCT/AU00/00399, filed on May 4, 2000.

(30) Foreign Application Priority Data

May 4, 1999  (AU) .............................................. PQ0152

(51) Int. Cl.$^7$ ............................................ G01N 27/333
(52) U.S. Cl. .................... 205/787.5; 204/433; 204/416; 427/58; 427/126.1
(58) Field of Search ................................ 204/416, 419, 204/403.01, 433; 205/787.5, 792; 427/58, 126.1

(56) References Cited

U.S. PATENT DOCUMENTS 4,507,194 A    3/1985  Shimomura et al.
4,561,963 A   12/1985  Owen et al.
5,480,534 A    1/1996  Kato et al.

FOREIGN PATENT DOCUMENTS

DE    114 866     8/1975
EP    0757246     2/1997
GB    2289541    11/1995

OTHER PUBLICATIONS

Caplus abstract for Gao et al, Chengdu Keji Daxue Xuebao, 1986, 2, pp. 73–78.*
Abstract for JP 10183029–A, Ishikawajima Harima Heavy Ind., Jul. 7, 1998.*
Abstract for SU 620390 A, Riga Med. Inst., Jul. 7, 1978.*
Mascini et al, Analytica Chimica Acta, 92 (1977), pp. 277–283.*
Caplus abstract for Mascini, Ion–Sel. Electrodes Conf. (1978), pp, 463–465.*

* cited by examiner

*Primary Examiner*—Kaj K. Olsen
(74) *Attorney, Agent, or Firm*—Oppedahl & Larson LLP (57) ABSTRACT

A pH electrode having a pH-sensitive region on an electrically conductive support, said pH-sensitive region comprising
  a mixture of
  between 50% and 85% of the total mixture by weight of particles of a Group VA or Group VIII metal incorporated in, or applied to, a polymer substrate of a non-shrinking plastic selected from polyimides, the polymer substrate having a resistivity of 10 to 100 Kohms/square
  the metal particles including antimony particles
  and, when said particles are incorporated into said resistive polymer substrate, having said pH-sensitive region abraded to expose said particles.

30 Claims, 10 Drawing Sheets

PH ELECTRODE AND METHODS OF PREPARING AND USING SAME

This application is a continuation-in-part of PCT Application No. PCT/AU00/00399, filed May 4, 2000 designating the United States, and is filed within 30 months of the priority date claimed in the PCT application. The PCT application is incorporated herein by reference.

BACKGROUND OF THE INVENTION

Antimony electrodes, and other electrodes formed from Group VA and Group VIII metals, have a number of potential advantages over other sensors. Antimony electrodes, in particular, can be small in diameter, robust, durable and inexpensive to produce. In addition, their relatively low impedance provides reduced electrical interference compared with miniature glass electrodes.

Development of the Present pH Probe
Early History

In 1923, it was known that certain metals in combination with their oxides could form the sensing component of a pH electrode, and antimony, with its trioxide, was suggested as being a suitable metal/metal oxide combination.

Since then, a few fundamental properties of the antimony (Sb) pH electrode have emerged.

First, it was obvious that the metal/metal oxide electrode was sensitive to the presence of oxidising substances, including oxygen. The electrical potential of the Sb electrode is normally negative to the reference electrode, and becomes more negative as the pH increases. The effect of oxygen reduces the output, making the potential less negative, giving the false indication that the test solution is more acid (lower pH) than it really is.

Another effect that has been reported is the formation of complex antimony compounds with ligands used in buffer solutions. Problem salts such as citrates, tartrates and oxalates are easy to avoid, but phosphates, also known to complex with antimony, are not so easily replaced in neutral buffers.

Some workers have reported that monocrystalline, and specially oriented, antimony gave more reliable results than non-crystalline material.

Development of the Antimony Electrode at the University of South Australia

In 1982, the School of Chemical Technology at the then SA Institute of Technology started work on ion-sensitive electrodes, including pH, using a rod of Teflon-filled graphite, approximately 12 mm in diameter. The end of this rod was sensitised with Bismuth or Antimony powder, either directly or glued to the end using a carbon-filled polymer paste (CFPP). This CFPP was actually a thick film resistor paste, ESL RS15115, which was known to have one of the lowest contents of silver in it. The paste had to be heat-cured to become hard.

By 1984, the electrode was made by simply printing the CFPP onto a ceramic substrate, omitting the Teflon-filled graphite rod. The electrode could now be made much smaller. The CFPP was first cured hard, and then sensitised by application of the appropriate powder to the wet paste.

In 1986, following some fairly thorough work on pH sensors, mainly miniature printed electrodes on ceramic substrates, it was found that antimony made a satisfactory pH electrode.

For medical purposes, the pH electrode had to be miniaturised further than would be possible on a ceramic substrate so, during 1991, an electrode was developed using insulated copper wire as the basic form, with an ion-sensitive end. A measuring meter was constructed, to go with this electrode. The present invention relates to further development of this electrode.

SUMMARY OF THE INVENTION

The pH electrode of the present invention has a pH-sensitive region, such as a pH-sensitive tip or head, comprising particles of a Group VA or Group VIII metal, in particular antimony, incorporated in or applied to a polymer substrate having at least a degree of electrical conductivity and, in particular, a resistivity of 10 to 100 Kohms/square. This pH electrode is mechanically robust, simple and accurate, at least under conditions of constant $pO_2$. Although $pO_2$ has an effect on the pH readings of this pH electrode, this can be overcome by appropriate calibration of the electrode.

References throughout to Group VA or Group VIII metals are inclusive of any oxide component which is present. For example, the antimony electrode of the present invention could more accurately be termed an antimony/antimony oxide electrode.

Accordingly in a first aspect of the present invention there is provided a pH electrode having a pH-sensitive region on an electrically conductive support, said pH-sensitive region comprising a mixture of between 50% and 85% of the total mixture by weight of particles of a Group VA or Group V/III metal incorporated in, or applied to, a polymer substrate of a non-shrinking plastic selected from polyimides, the polymer substrate having a resistivity of 10 to 100 Kohms/square the metal particles including antimony particles and, when said particles are incorporated into said resistive polymer substrate, having said pH-sensitive region abraded to expose said particles.

The pH-sensitive region comprises between 50% and 85% of the total mixture by weight, more preferably between 60% to 80%, most preferably between 70% and 75% of particles of a Group VA or Group VIII metal; and between 15% and 50% of the total mixture by weight, more preferably between 15% and 30%, most preferably between 20% and 25%, of a polymer substrate of a non-shrinking plastic selected from polyimides.

In a further preferred form the polymer substrate includes between 5% to 20% of the total mixture by weight, preferably 5% to 15%, more preferably 5% to 10%, of carbon black.

Preferably the pH sensitive region comprises a mixture of the metal particles incorporated into the polymer substrate.

In a further preferred embodiment, the pH-sensitive region forms a band extending around a tubular support.

In a further aspect of the present invention, there is provided a method for preparing a pH electrode comprising formation of a pH-sensitive region on an electrically conductive support by applying thereto a polymer substrate of a non-shrinking plastic selected from polyimides, having a resistivity of 10 to 100 Kohms/square, said polymer substrate comprising between 50% and 80% of the total mixture by weight of particles, of a Group VA or Group VIII metal incorporated therein or applied thereto either before or after application of said polymer substrate to said support, the polymer substrate having a resistivity of 10 to 100 Kohms/square the metal particles including antimony particles and, when said particles are incorporated into said resistive polymer substrate, having said pH-sensitive region abraded to expose said particles.

According to a third aspect of the present invention, a pH electrode of the present invention is used to measure pH, in particular the pH of:

a) body fluids—eg extracellular fluid, blood, lymph, cerebro-spinal fluid b) muscle—eg cardiac muscle, skeletal muscle, smooth muscle c) the gastrointestinal tract—eg oral cavity, pharynx, oesophagus, stomach, small intestine, colon, biliary tract d) the respiratory tract.

DETAILED DESCRIPTION OF THE INVENTION

The present invention will now be described in more detail with respect to specific embodiments, which are illustrative but not restrictive of the present invention. In these embodiments, antimony is being used as the Group VA metal. However, other suitable metals may be included, such as platinum or ruthenium (Group VIII) or bismuth (Group VA).

In a preferred embodiment, the first part of the electrode consists of an insulated wire, the insulation being preferably polyurethane because of its strength and biocompatibility, and the wire being metallic, and preferably copper for economy. The diameter of the wire will generally fall between 0.2 mm and 0.5 mm. The length can be as long as desired or convenient.

One end of the wire will usually be prepared for an electrical connection to the measuring apparatus. The other end of the wire supports the novel pH-sensitive head of the present invention, connected to the copper core.

The pH-sensitive head is formed by applying, to a small section of bare copper, a very small amount of an adhering mixture of polymer paste containing particles of pure antimony metal, or applying a thin layer of antimony powder to the sticky uncured polymer paste.

The polymer paste is partially electrically conductive (eg with a resistivity of approximately 100 ohms per cubic centimetre) when cured. This polymer paste can be any non-shrinking adhesive plastic polymer, such as an appropriate polymer made slightly conductive with carbon (eg graphite) and/or silver, for example, a polyamide filled with carbon and traces of sliver.

The size of the antimony particles is important, the maximum dimension preferably being 50 microns, and there being no minimum. The amount of antimony in the polymer paste is preferably between 50% and 80%, and more preferably between 60% and 70%, of the total mixture by weight.

An early version of the pH electrode of the present invention, although relatively crude, was still effective. This early version was a metallic (eg copper) wire, with a pH sensitive head at one end, comprising an adhesive polymer with particles of antimony powder attached thereto.

In a particular embodiment of this early version of the electrode, a polyurethane insulated copper wire, with an overall diameter of 0.41 mm, was cut to a length depending on the intended use.

The wire was then "tinned" in molten solder, for about 10 mm at one end, and 1–2 mm at the other end. As polyurethane insulation is specially formulated to vaporise at 350° C., all that is necessary for clean "tinning" is to dip the insulated wire in molten solder at slightly above 350° C.

The short "tinned" end was covered in a thick film resistor paste (ESL RS 15115), eg by dipping and twisting, to obtain the minimum amount required for full cover.

While the paste was still wet, antimony powder was applied, eg by "sprinkling", dusting or by dipping the wet-paste-covered end into the metal powder.

The antimony covered electrode was then baked in an oven, eg for two hours at 150° C., to cure the paste.

Early versions of this electrode often had a rather rough looking sensor head, because the antimony powder had not been graded to any particular size, and the head had a slightly greater diameter than that of the insulated wire. There was also some difficulty with regard to non-uniformity between electrodes.

The first step in improving the performance of the electrode was to access a supply of high quality antimony powder.

The second improvement was to sieve the metal powder to limit the maximum size of the metal particles. A 400× mesh has been found to be suitable, limiting the largest particle size to about 50 microns, and resulting in an electrode with a relatively smooth surface. The unsieved powder had particles of up to 0.6 mm in length, resulting in a very rough final surface.

A further improvement was to introduce a measure of uniformity into the product, by controlling the shape of the pH-sensitive head. A cone shape was found to be suitable and, during development, the cone was made shorter, reducing to a "bullet nose", in order to reduce the amount of antimony, and thereby reduce any possible toxic effects.

An additional improvement was to actually mix the antimony powder into the paste, and then apply this paste/metal mixture to the preformed end of the wire.

A final improvement was to grind the outer surface of the cured mixture, to expose a smooth Terrazzo-like surface of metal particles.

A particularly preferred embodiment of the present invention is the so-called "Terrazzo Tipped Electrode", which incorporates all of the abovementioned improvements. The "Terrazzo Tipped Electrode" is described in more detail below.

In this preferred embodiment, where the pH-sensitive head comprises a polymer/antimony mixture, that uncured mixture is applied to the end of the copper wire, to form a minute ball with a diameter of no more than 1½ times the diameter of the insulated wire. The polymer/antimony mixture is then cured according to the requirements of the polymer. A typical curing schedule is two hours at 150° C.

The cured ball, comprising a mixture of hard polymer and antimony metal, together with its length of wire, may be spun in a microlathe, where a large part of the outer surface of the ball is removed, eg by grinding with a fine emery paper. The size of the grit in the emery paper is of the order of 1,000. It is important that none of the copper core of the wire is exposed.

Under the microscope, the final appearance of the ground surface of the pH-sensitive head is that of shiny metal pieces in a black matrix, very much like a Terrazzo surface.

The advantages of this particular embodiment of the invention (ie the Terrazzo-tipped electrode) are that the antimony particles are held much more firmly onto the end of the electrode than if the antimony powder is merely applied to the polymer surface; the tip is much smaller, thereby being less intrusive in clinical use; the smoother tip is also better for clinical use; and the smaller amount of antimony presents a lesser toxic hazard.

This method of making the Terrazzo electrodes provides a product having very consistent performance.

The smooth surface of the Terrazzo electrode is suitable for the application of a film formed from an oxygen barrier polymer, whereby the difficulties associated with oxygen sensitivity can be overcome.

Extensive testing has been carried out on the earlier version of the pH electrode of the present invention (ie the electrode having antimony powder applied to the surface of the paste-covered end of the wire), and the results of that testing are set out below. The performance of the Terrazzo Tipped Electrode has since been tested, with similar or better results.

The present invention will now be more fully described with reference to the accompanying examples and drawings. It should be understood, however, that the description following is illustrative only and should not be taken in any way as a restriction on the generality of the invention described above.

EXAMPLE 1

Figure 1:
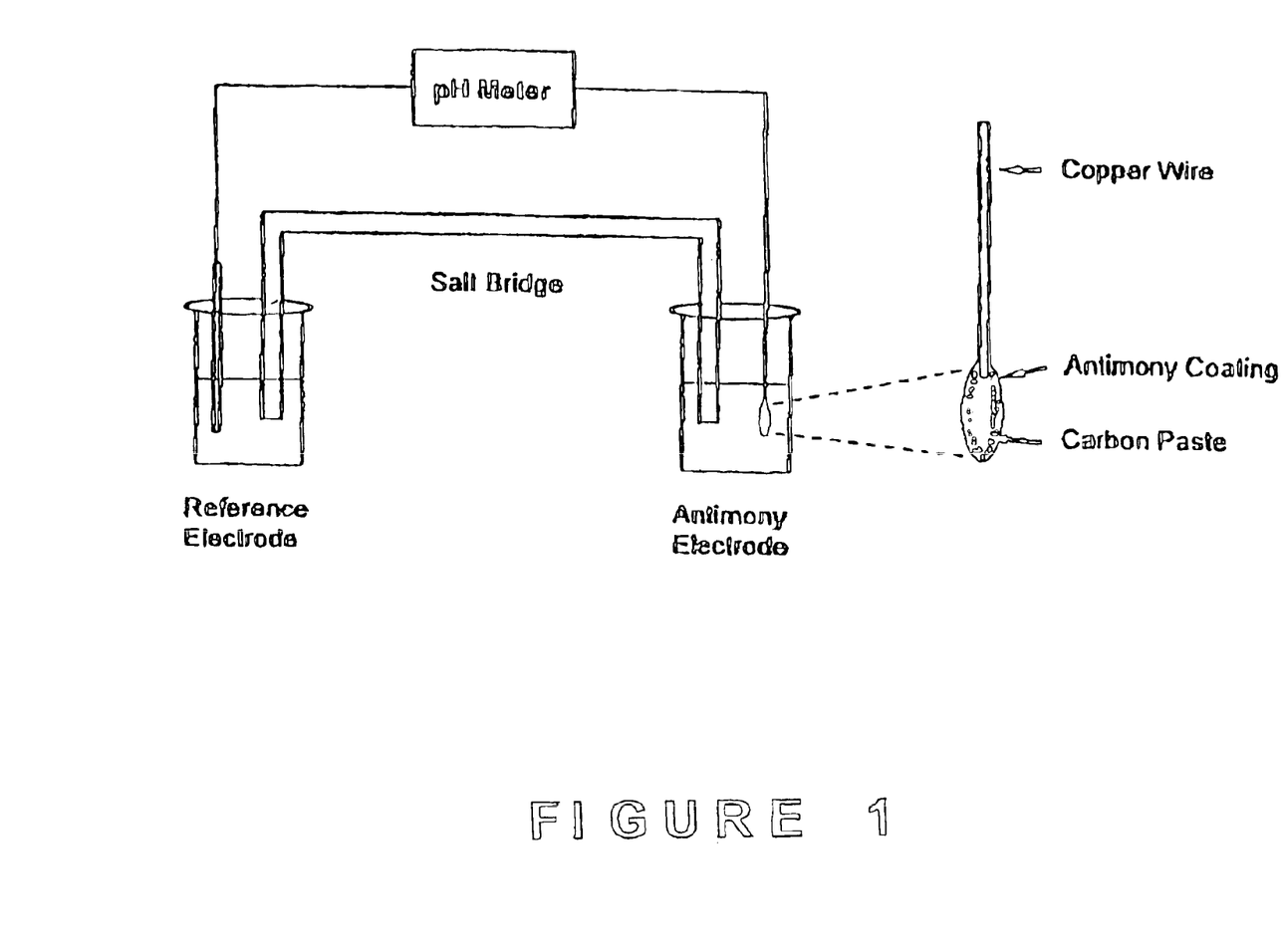
FIG. 1: An early version of the antimony electrode comprises a coating of antimony powder on carbon-filled polymer paste applied to copper wire. A salt bridge links the test solution and the reference electrode. A conventional pH meter is used for measuring the potential from the antimony sensor.

An embodiment of the pH electrode according to the present invention is constructed as follows:

The 3-step process is diagrammatically illustrated in FIG. 1.

Step 1

A mould including a cavity of generally circular cross-section is provided. An electrical conductor (e.g. copper wire) passes generally centrally through the base of the cavity and extends a small distance into the cavity interior.

A "liquid antimony" composition is prepared having a composition as described in Table 1 below.

Step 2

The liquid antimony (antimony containing carbon-filled polymer paste) is dispensed into the cavity via a syringe and is subsequently cured (e.g. heat cure at 150° C. for approximately 2 hours).

Step 3

The upper exposed layer of the cured antimony containing polymer paste is then subjected to a grinding and polishing step.

The liquid antimony composition has the following constituents:

TABLE 1

| Liquid antimony composition | |
|---|---|
| Component | % by weight |
| Antimony (Sb) powder (99.8% pure) | 80 |
| Polymer paste CMI 121-40 | 20 |

Raw Material Specifications for Liquid Antimony

Specifications of raw materials used in the current product are detailed below, alternative materials of similar specifications (purity, resistivity) could be used for construction of pH sensors with similar physico-chemical properties.

Antimony (Sb) Powder

Product of Merck Chemicals, Frankfurt, Germany.

Product code 107832

Minimum purity 99.8% (As 0.005%, Cu 0.005%, Fe 0.01%, Pb 0.005%)

Particle size <150 μm

Polymer Paste: Carbon-filled, Polyimide Based, Resistive Ink

Product of Creative Materials Inc. Tyngsboro, Mass., United States of America, Product code CMI121-40*

121-40 is a high temperature resistant, carbon filled, polyimide based coating for application by screen printing, dipping and syringe dispensing. The product features excellent adhesion to polyimide (Kapton®), glass and a variety of other substrates. Unlike conventional conductive materials, this product is very resistant to abrasion and scratching. Some applications for 121-40 include, but are not limited to, printed resistors, potentiometers, emi/rfi shielding of polyimide flexible circuits, polymer thick film circuitry, and membrane switches.

Properties

| | |
|---|---|
| Viscosity (cps) | 11000–13000 |
| Volume resistance (Ω-cm) | 25 |
| Sheet resistivity (Ω/square/mil) | 10000 |
| Hydrolytic stability | Excellent |
| Useful temperature range | −55 to 210° C. |
| Boiling point | >325° C. |
| Specific gravity (water = 1) | 1.2 |

Ingredients

75–85% proprietary resin and solvent (details undisclosed)

5–15% by weight carbon black (CAS#1333-86-4)

*CM1-121-40 is carbon-filled, polyimide based, resistive ink that has a sheet resistivity of 10000Ω/square/mil.

Preparation of Liquid Antimony

Step 1: Antimony powder, is passed through a stainless steel sieve with hole size of 65 microns, and only the particles that fall through are used.

Step 2: A unit quantity of the resistive polymer is weighed on an accurate balance, in a mixing pan.

Step 3: The sieved antimony powder are added to the polymer, and thoroughly mixed into the polymer, forming a liquid antimony mixture.

Step 4: This liquid antimony is placed in a small hypodermic syringe and is then ready to use.

Figure 2:
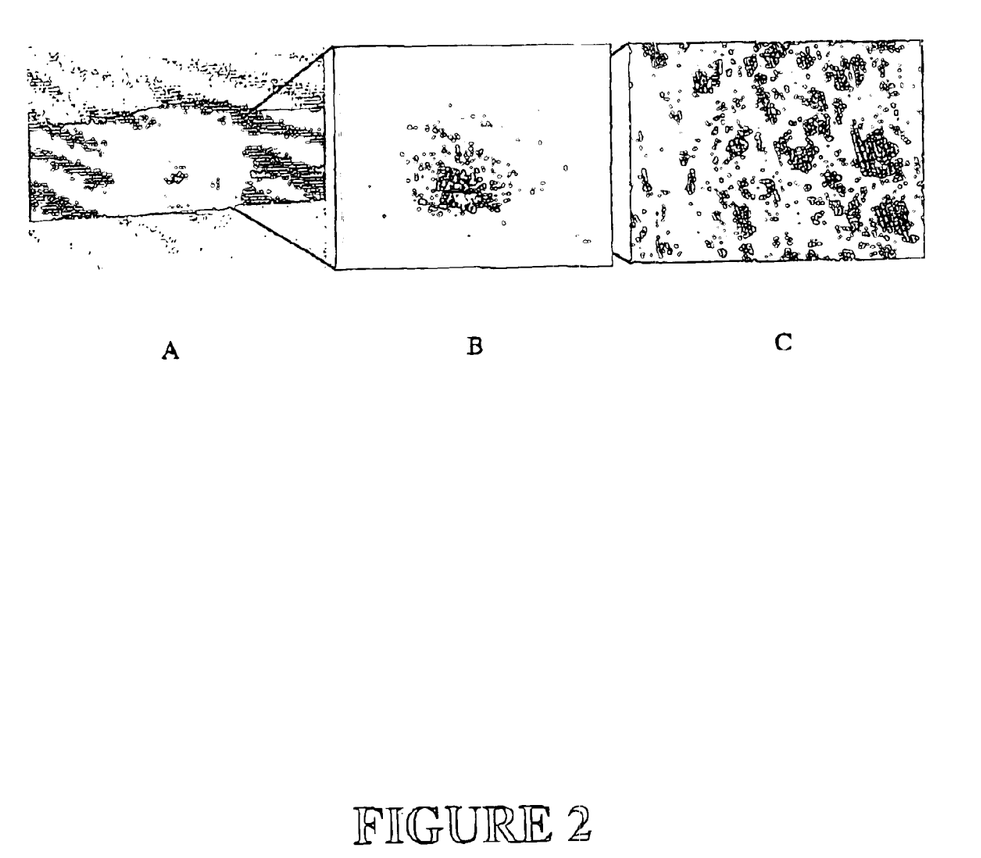
FIG. 2A: An embodiment of the pH electrode under ×5 magnification.
FIG. 2B: An embodiment of the pH electrode under ×10 magnification.
FIG. 2C: An embodiment of the pH electrode under ×50 magnification.

The resultant exposed pH electrode surface is illustrated in FIGS. 2A to C.

FIG. 2A illustrates an embodiment of the pH electrode under x5 magnification.

FIG. 2B illustrates an embodiment of the pH electrode under x10 magnification.

FIG. 2C illustrates an embodiment of the pH electrode under x50 magnification.

Individual generally rhomboid-shaped Sb crystals are apparent surrounded by darker areas of cured polymer paste forming the electrical connection between crystals in the matrix.

EXAMPLE 2

In a second embodiment of a pH electrode according to the present invention, Example 1 is repeated except that a band or tube of the liquid antimony composition is formed on the tubular support and extends around the surface of a tubular support. The tubular support may be formed from any suitable plastics material which will withstand the temperatures required to cure the liquid antimony composition. A polyimide, a polyurethane or a polyether-block-amide (eg PEBAX) have been found to be suitable.

Figure 3:
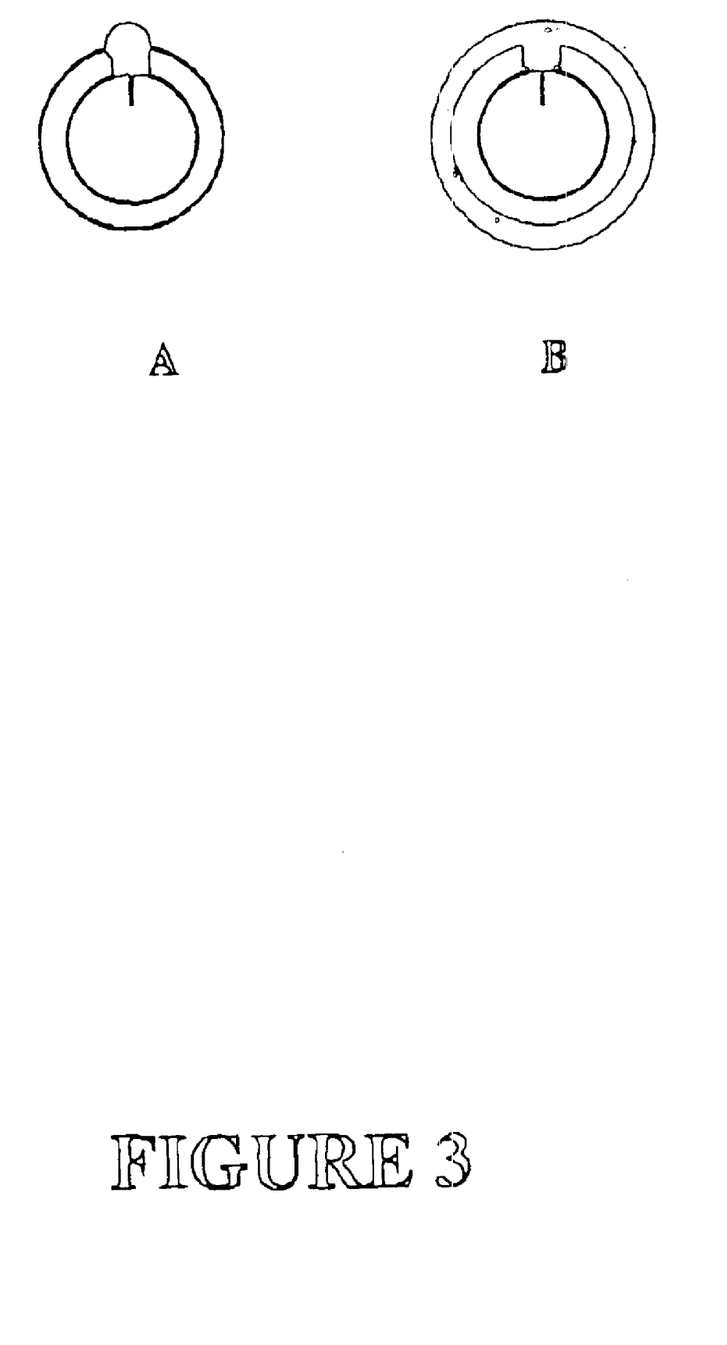
FIG. 3A: A schematic illustration of an embodiment of the radial pH electrode according to the present invention.
FIG. 3B: A schematic illustration of a standard single point pH electrode as in FIG. 2.

A radial pH electrode is illustrated schematically in FIG. 3B (FIG. 3A illustrates schematically the standard single point pH electrode of Example 1).

Figure 4:
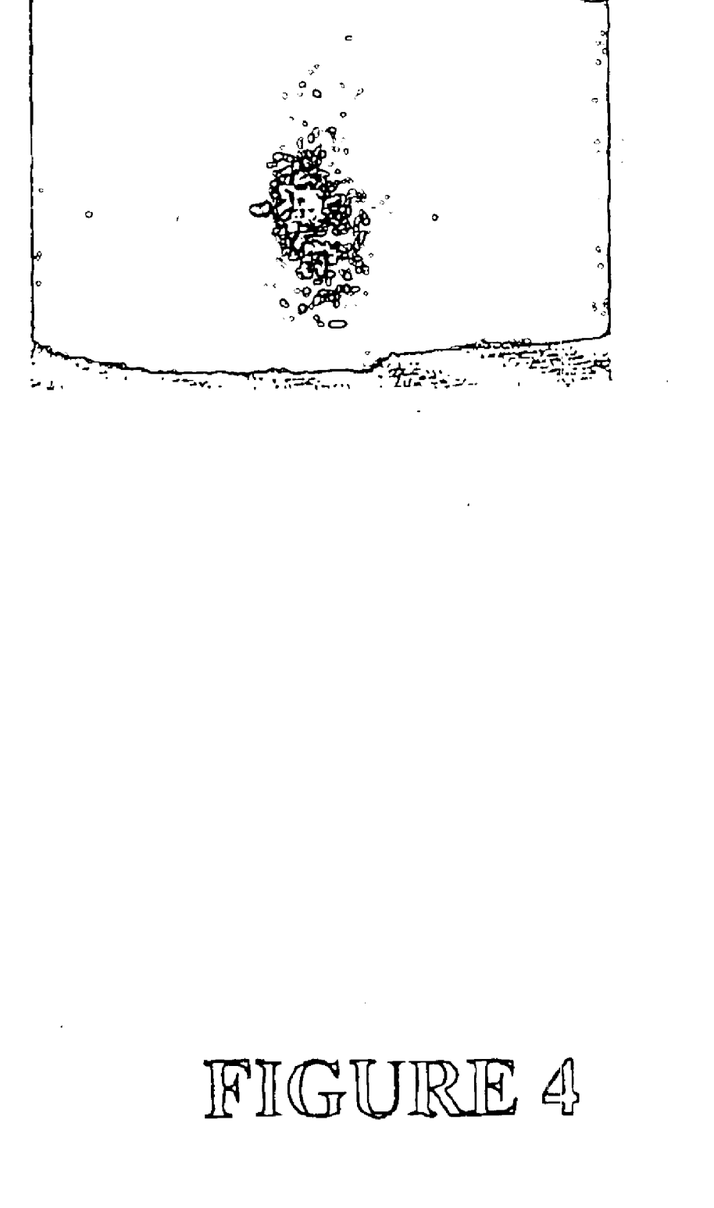
FIG. 4: A photomicrograph of an embodiment of the radial pH electrode.

FIG. 4 is a photomicrograph of an embodiment of the radial pH electrode.

EXAMPLE 3

Testing of the pH Electrode

The pH electrode of the present invention was tested, using a silver-silver chloride electrode (Activon AEP113, NSW. Australia) as a reference electrode. A salt bridge composed of silicone rubber tubing (40 cm in length, 2.5 mm in ID) filled with 3% agar saturated with potassium chloride solution connected the test solution and the reference electrode to complete the electrical circuit (FIG. 1). A pH meter (Cyberscan 2000, Eutech Cybernetics, Singapore), set to read millivolts, was used for measuring the potential from the antimony sensor. The conventional glass electrode of the Cyberscan 2000 pH meter was used as the standard to determine the true pH of the solution.

Pilot studies in rates suggested that oxygen would have a major confounding effect on in vivo pH measurement with antimony electrodes. Therefore a multifunctional monitoring probe system (Paratrend 7, Biomedical Sensors Ltd, UK) was used in the present experiments to determine the pH, $pO_2$ and $pCO_2$ of the bloodstream and the myocardium alongside the antimony electrode under test. The Paratrend has been verified as a reliable device for measuring pH and gas tension in blood and tissue and is in regular clinical use The values for blood pH obtained from the Paratrend were checked against those from a pH/blood gas analyser (System 1306, Instrumentation Lab Inc, USA) throughout the experiments.

In Vitro Testing in Phosphate Buffers and Human Blood Samples

To assess the basic properties of the antimony electrode, in vitro tests were conducted with freshly prepared 0.1 M phosphate buffer (pH 6.2–7.8) and in samples of human blood of various pH levels. Antimony and glass electrodes were calibrated in the same standard reference solutions (Sigma Chemical Co). The sensitivity and accuracy of the antimony electrodes for measuring pH were examined. Simultaneous measurement with a conventional glass electrode was carried out. The stability of the antimony electrodes over time was determined by re-testing after leaving the electrode exposed to the air for 1, 3, 7 and 14 days.

The influence of temperature on the response of the antimony electrode was evaluated in 0.1 M phosphate buffer. The buffer was warmed from 10° C. to 40+ C. and changes in potential readings for both the glass electrode and the antimony electrode were recorded. Using the data of temperature vs potential for the antimony electrode, a computerised algorithm was developed to compensate for the effect of the temperature on the electrode.

To assess the interfering effect of oxygen on the antimony electrode, the oxygen tension of the phosphate buffers was gradually elevated by bubbling oxygen into the solution and lowered by bubbling nitrogen. The pH values at different oxygen levels were measured with the antimony electrode and compared with the values obtained simultaneously using the glass electrode.

Figure 5:
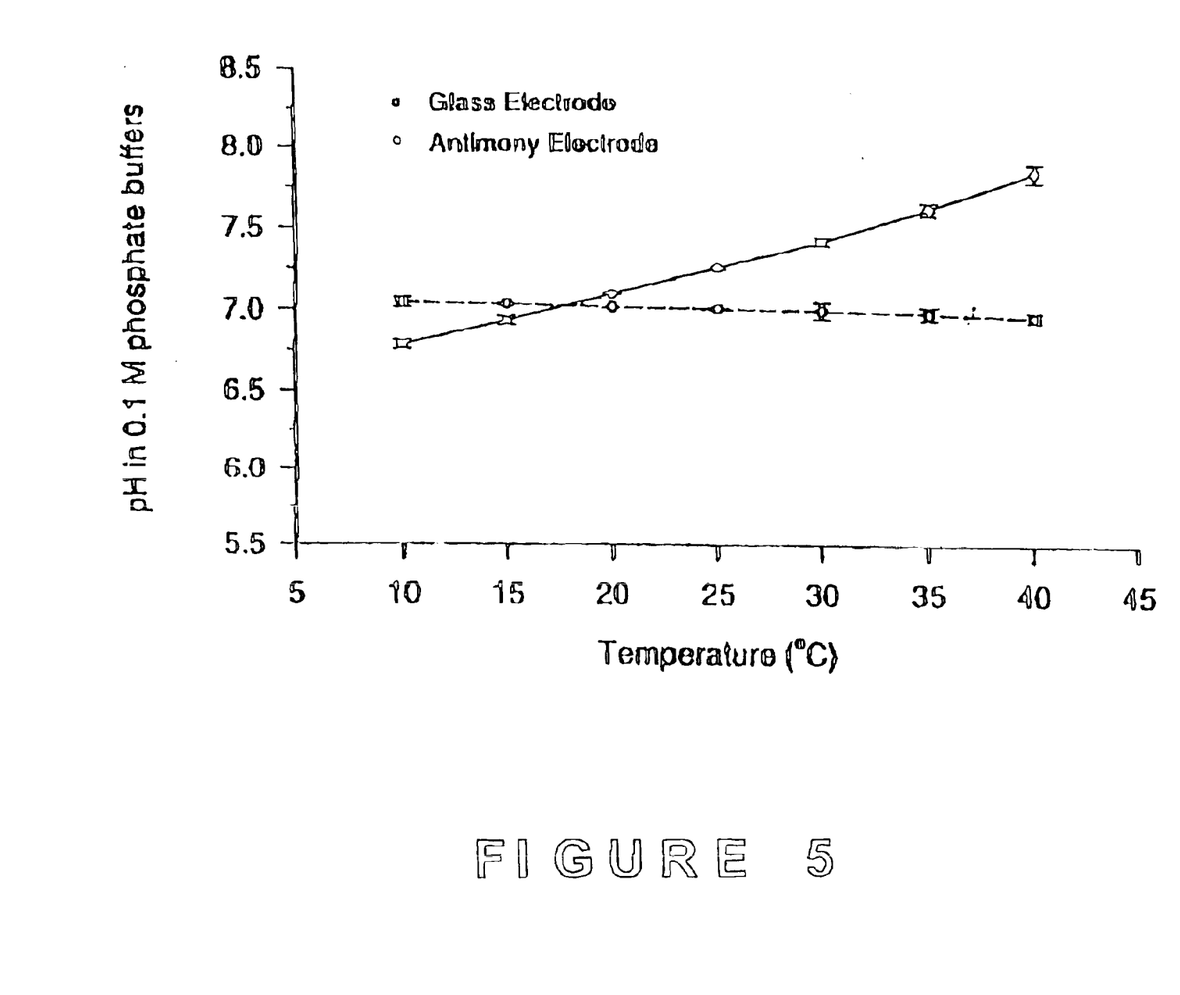
FIG. 5: The effects of temperature on the antimony electrode and the conventional glass electrode. Each data point on the antimony electrode line represents the mean values from four electrodes. With the antimony electrode, the variation of pH with temperature was $0.03 \pm 0.002$ pH/° C., whereas that measured for the glass electrode was $-0.01 \pm 0.004$ pH/° C. ($p<0.001$).

The characteristic response of five antimony electrodes to pH in buffers showed that the potential decreased linearly as the pH of the solution increased. The average gradient was −50.2±1.8 mV/pH at 25° C. ($r^2$=0.98). Slight differences were observed in both slope and intercept between individual electrodes. Under conditions of constant temperature and $pO_2$, the pH reading with the antimony electrode in phosphate buffer was very close to the reading with the glass electrode. Over a pH range of 6.2 to 7.8, a strong correlation ($r^2$=0.97) was observed with a mean difference between paired observations of only 0.027±0.004 pH units. In blood samples at constant $pO_2$, the results were almost identical to those in phosphate buffer, with a difference between paired observations of the antimony and glass electrodes of only 0.067±0.014 pH units. The sensitivity of electrodes was almost the same over 7 days, with only a slight decrease in the slope at 14 days (−50.2 to −48.6 mV/pH). After several weeks, the response time of the probe increased (from 6–8 seconds to several minutes) and there was a tendency for drift to occur during measurement. When the phosphate buffer was warmed, the pH reading from the antimony electrodes increased whereas the pH measured by the glass electrodes decreased (FIG. 5). A greater temperature effect was observed for the antimony electrode than for the glass electrode. With the antimony electrode, the variation of pH with temperature was 0.03±0.002 pH/° C. within the temperature range of 10° C. to 40° C., whereas the variation in pH measured by the glass electrode was much less: −0.01±0.004 pH/° C. (p<0.001; FIG. 5). When computerised temperature compensation was used with the antimony electrode, the readings were very similar to those from the glass electrode, with a difference of less than 0.08 pH units within the temperature range 10° C. to 40° C.

A marked effect of oxygen on the measurement of pH in phosphate buffer was found with the antimony electrode, the pH reading decreasing as $pO_2$ increased in a non-linear fashion. $pO_2$ had a greater effect in the lower range of $pO_2$. Logarithmic transformation revealed a linear relation ($r^2$=0.96) between $pO_2$ and potential (FIG. 6), with a slope of 0.73 pH/log $pO_2$ (mmHg). In contrast, for the glass electrode, the pH reading was unaffected by changes in $pO_2$ in phosphate buffer.

Bloodstream pH

Four greyhound dogs weighing 28–32 kg were anaesthetised with pentobarbital (25 mg/kg), intubated and mechanically ventilated. The antimony electrode and the Paratrend probe were inserted into the femoral artery. The pH of the bloodstream was measured with the antimony electrode and with the Paratrend. $pO_2$ and $pCO_2$ in the bloodstream were monitored by the Paratrend system. Blood samples were collected periodically from the femoral artery and measured with the pH/blood gas analyser for validation of the value obtained from the Paratrend. All animal experimentation was conducted under the guidelines for animal experimentation of the National Health and Medical Research Council of Australia. Protocols were approved by the institutional ethics committee of the Baker Medical Research Institute, Prahran, Victoria. After the baseline readings, the blood pH was lowered by ventilating the dog with increasing amounts of $CO_2$ and elevated by intravenous injections of sodium bicarbonate. The pH changes were monitored by the antimony electrode and the Paratrend. To determine the effect of oxygen on these electrodes in the bloodstream, the oxygen tension of the bloodstream was altered by ventilating with various concentrations of oxygen or nitrogen.

Figure 7:
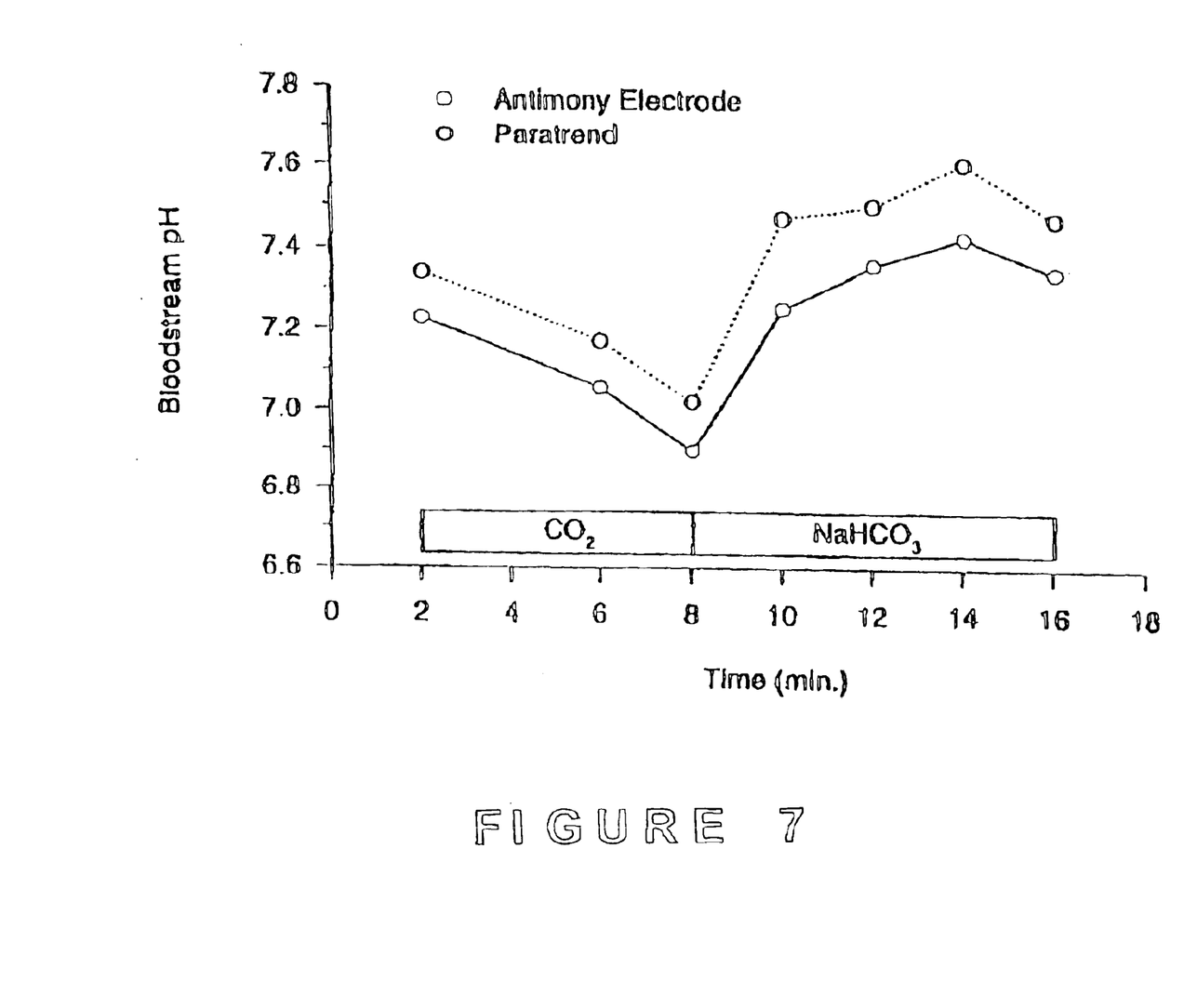
FIG. 7: A typical example of pH measurement with the antimony electrode and a reference Paratrend probe in the bloodstream of a dog. The alternation in blood pH was achieved by ventilating the dog with $CO_2$ or by injecting sodium bicarbonate intravenously. There is a constant offset of approximately 0.15 pH unit between readings from the antimony electrode and the Paratrend.

When bloodstream pH and gas partial pressures measured with the Paratrend were checked against the reading from the blood gas machine as the standard, close agreement was found ($r^2$=0.99), indicating a true reading of blood pH by the Paratrend. Both the antimony electrode and the Paratrend showed a decrease in pH when ventilating the dog with $CO_2$, and an increase in pH when injecting sodium bicarbonate intravenously. However, a constant offset of approximately −0.15 pH unit was found between the measurements from the antimony electrode and the Paratrend. A representative result is shown in FIG. 7. Thus the antimony electrode readings were below the true pH. This might reflect the effect of oxygen on the antimony electrode, since the antimony electrode was calibrated in the phosphate buffer at 150 mmHg of $pO_2$ but used in the bloodstream at $pO_2$ level above 200 mmHg, which would falsely lower the pH reading.

When the dogs were ventilated with increasing concentrations of oxygen, an increase in blood $pO_2$ was observed with the Paratrend and the blood gas analyser. Blood pH, as measured continuously by the Paratrend and checked frequently by the blood gas analyser, changed little. By contrast, the blood pH measured with the antimony electrode decreased dramatically as the blood $pO_2$ increased. The greatest interfering effect of oxygen on the antimony electrode readings was in the lower $pO_2$ range, as had been observed during in vitro testing. The Paratrend and the antimony electrode had almost the same pH reading in the blood at a $pO_2$ level of 150 mmHg, which was the oxygen content of the phosphate buffer used for calibrating the antimony electrode.

Myocardial pH

The heart was exposed via a left thoracotomy. The antimony electrode was tunnelled into the anterior left ventricular wall near the apex. The Paratrend probe was introduced into the myocardium close to the antimony electrode. The reference electrode was placed in saturated KCl solution and linked to the body via a salt bridge terminating in a subcutaneous pocket. Systemic blood pH and oxygen level were varied as described previously by altering carbon dioxide, oxygen and sodium bicarbonate levels in the bloodstream. Myocardial ischaemia in the region of the two sensors was induced by occluding the left anterior descending coronary artery. After 10 minutes, the occlusion was released. Myocardial pH was measured with the antimony electrode; myocardial pH, $pO_2$ and $pCO_2$ were monitored with the Paratrend.

Figure 8:
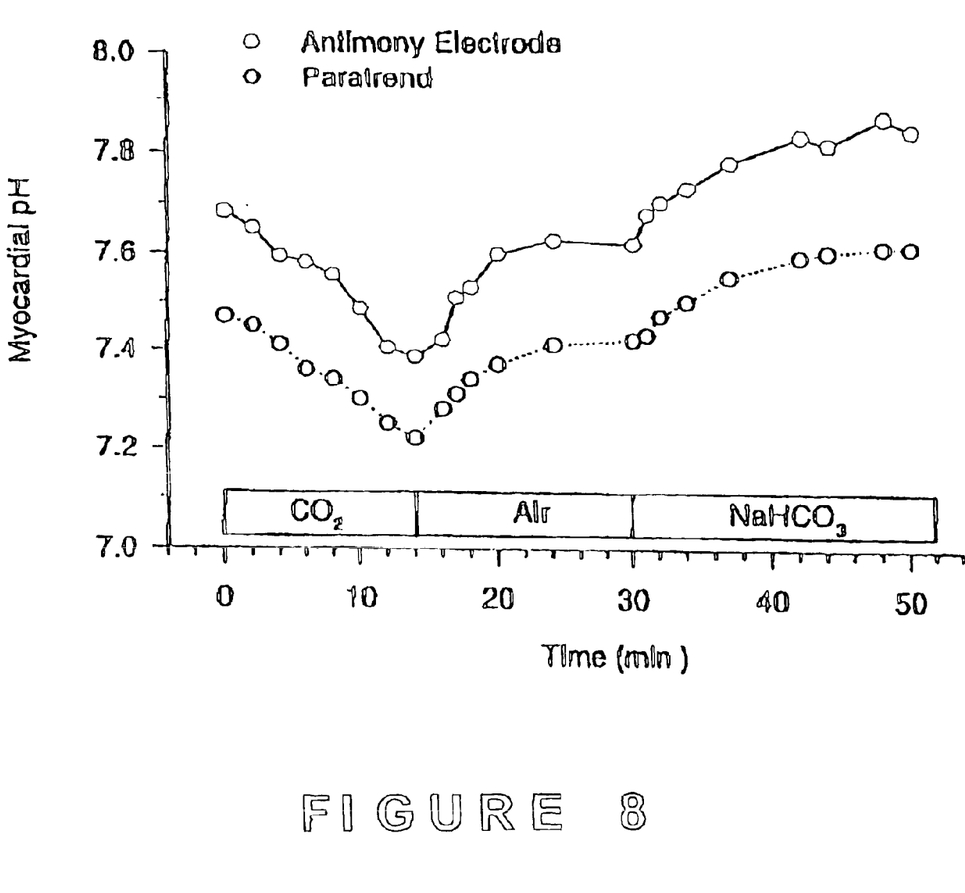
FIG. 8: A typical example of pH measurement with the antimony electrode and the Paratrend in the myocardium of a dog. Increases in ventilating $CO_2$ volume to the dog resulted in decreased myocardial pH, and injecting sodium bicarbonate intravenously resulted in Increasing the pH, as read by both the Paratrend and the antimony electrode. There is a constant pH offset between readings from the antimony electrode and the Paratrend.

By ventilating with $CO_2$ or injecting sodium bicarbonate, marked changes in myocardial pH were achieved. Increases in inspired $CO_2$ concentration resulted in decreased myocardial pH as indicated by the Paratrend electrode (FIG. 8). Conversely, infusion of sodium bicarbonate increased the myocardial pH. At constant $pO_2$, the pH readings from the antimony electrode exhibited a similar pattern to the Paratrend. As in the bloodstream there was a constant offset between the pH readings of the Paratrend and the antimony electrode. In this case, the antimony electrode reading was approximately 0.26 pH unit higher than that measured with the Paratrend as in the bloodstream. This could be accounted for by the interfering effect of oxygen. The $pO_2$ in the myocardium during these measurements was lower than the $pO_2$ of 150 mmHg at which the antimony electrode was calibrated, and would thus falsely raise the pH reading.

Figure 6:
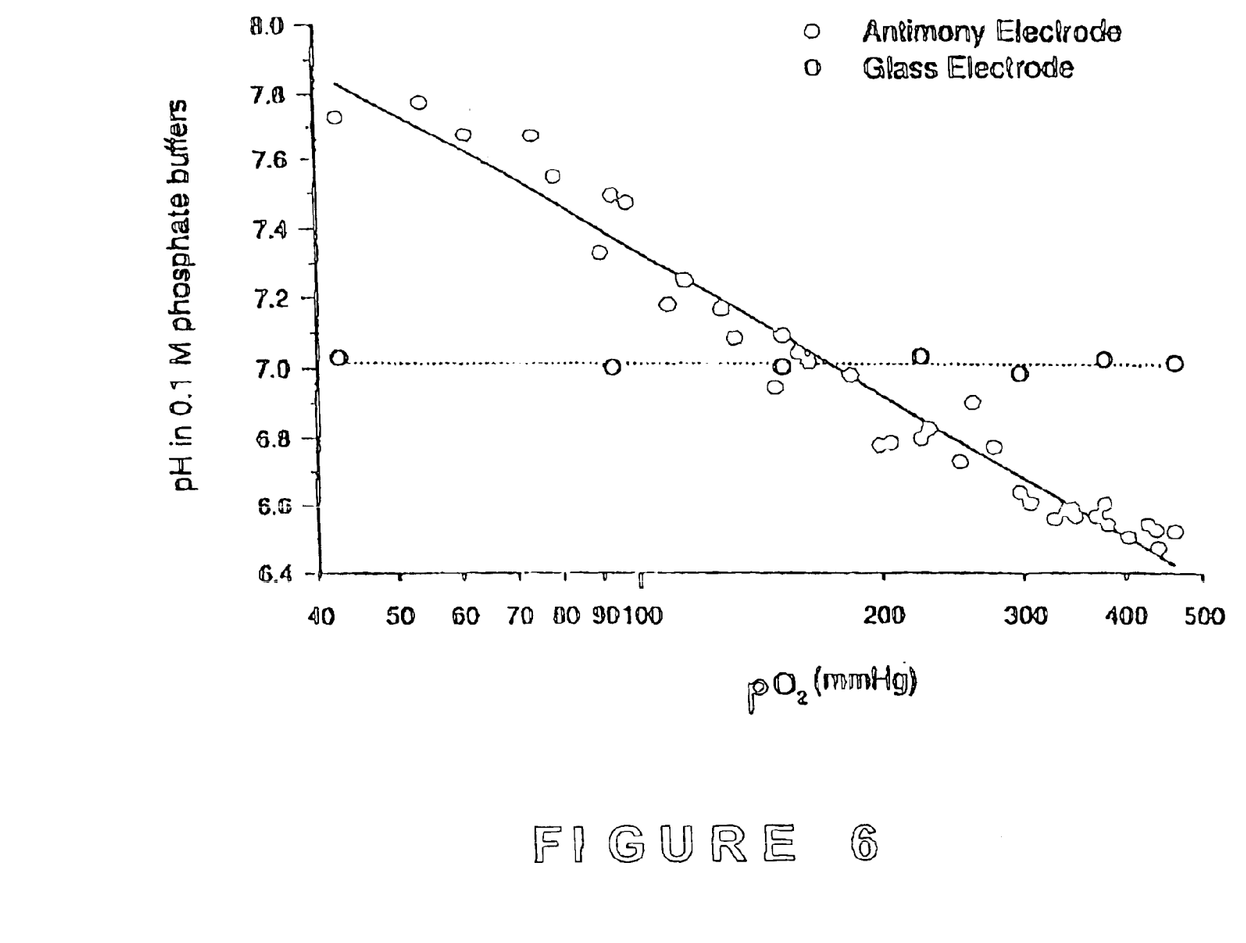
FIG. 6: The influence of oxygen on the pH measurements with the antimony electrode and glass electrode in pH 7.0 phosphate buffer. The pH measurement with the glass electrode is not affected by oxygen. A marked influence of oxygen on pH measurement is seen with the antimony electrode. Logarithmic transformation revealed a liner relation ($r2=0.96$) between $pO_2$ and potential.
Figure 9:
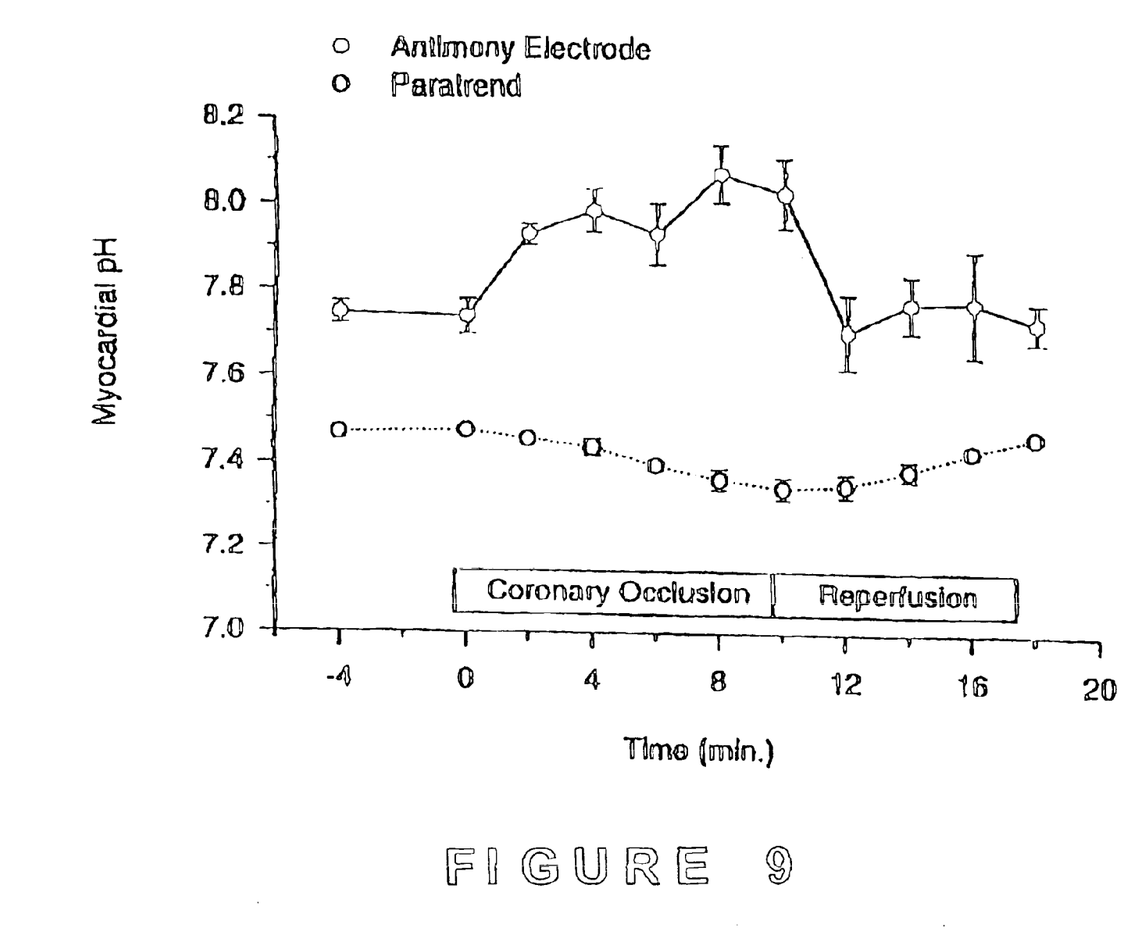
FIG. 9: pH measurement with the antimony electrode and the Paratrend during myocardial ischaemia and reperfusion. As expected, when measured by the Paratrend, during a 10 minute coronary artery occlusion, myocardial pH gradually decreased and, during reperfusion, the pH returned towards the base-line. Paradoxically, as measured by the antimony electrode, the pH increased during coronary occlusion and decreased during reperfusion.

During the 10 minute coronary artery occlusion, as monitored by the Paratrend, myocardial pH and $pO_2$ gradually decreased and $pCO_2$ increased, as would be expected (FIG. 9). During reperfusion, myocardial pH, $pO_2$, and $pCO_2$ returned towards the baseline levels. The average pH was lowered by 0.013 pH units (7.47±0.008 vs 7.34±0.03, p<0.01 n=4). In contrast, myocardial pH readings from the antimony electrode showed the opposite effect, the pH reading increased following coronary artery ligation and decreased during reperfusion (FIG. 6).

Oesophageal pH

The antimony electrodes of the present invention were tested for measurement of oesophageal pH, which is an important component of the clinical evaluation of gastro-oesophageal reflux disease (GORD).

GORD occurs when the amount of acid welling up from the stomach into the oesophagus is sufficiently great to cause damage to the mucosal lining of the oesophageal lumen; a condition known clinically as oesophagitis.

The antimony pH probe of the present invention has been evaluated for measurement of oesophageal pH to enable recognition of intra-oesophageal drops in pH associated with episodes of gastro-oesophageal reflux (GOR).

The events recorded are usually in the pH range of 1–5. The general criteria used to recognise GOR episodes are the identification of pH drops from above to below pH 4 that are greater than 1 pH unit in magnitude. Other parameters of interest are the GOR clearance time; time taken for oesophageal pH to return to a level of 4 or above after a GOR episode; and the reflux index (ie the % of total time that oesophageal pH remains below 4). Normal values for reflux index are usually below 4% if measured over a 24 hour period.

Testing of the antimony pH sensors indicates that they have a performance similar to control pH probes, namely Synectics pH electrodes. The pH sensors accurately sense pH within the physiological range (pH 1–7), have good stability over several hours and a 90% response time of <10 sec. The Synectics pH 1 buffer (presumably a HCl/KCl buffer) and a pH 7 potassium phosphate/sodium phosphate buffer (Micro Essential Laboratory) were used for the purpose of calibration of sensors.

Our initial experience with oxalate, citrate and tartrate buffers was that they caused irreparable damage to the probes and could not be used.

The probes are small enough (0.2 mm o.d.) to install into a manometric assembly (device for measuring pressures within the oesophagus) or can be fashioned into stand-alone probes that can be used in conjunction with commercially available pH meters.

The degree of miniaturization of the pH sensors (to an o.d. of 0.2 mm) has enabled studies of GOR in very premature neonates. These studies have never before been performed because existing pH electrodes are prohibitively large in size (over 1 mm in diameter).

The apparent oxygen sensitivity of the pH sensors was not considered to be an issue of major importance because the existing commercially available probes were evaluated and found to be similarly oxygen sensitive. Furthermore, the oxygen content of gastric juice is unlikely to fluctuate significantly.

In order to further evaluate the pH sensors, a series of In vivo comparative studies were performed where both a commercially available probe (the Medtronic probe) and a probe of the present invention were placed side-by-side at the same location within the oesophageal body. The aim of this trial was to validate the clinical use of the pH sensors for the diagnosis of gastro-oesophageal reflux disease.

Nineteen patients requiring a 24 h oesophageal pH monitoring study for diagnoses of reflux disease were enrolled. To allow for a simultaneous comparison of the different probes, a purpose built interface allowed the pH readings to be simultaneously recorded by a datalogger (Medtronic 'Digitrapper'). The patients were studied after an overnight fast and were intubated with both pH probes using standard techniques for clinical diagnostic procedures and the probes were positioned 5 cm above the lower oesophageal sphincter.

At the completion of the 24-hour study oesophageal pH recordings were analysed using the Medtronic 'Esophagram' data analysis software and the normal/abnormal diagnostic outcomes were compared.

In all studies, pH probes of the present invention rendered the same normal/abnormal diagnostic outcome as the standard probes. Reflux parameters calculated for the total recording were also similar. Hence pH probes of the present invention were found to be diagnostically equivalent to the standard probes.

Measurement of Antimony in Plasma

Antimony release from the electrode into human blood was assessed in vitro. The antimony and reference electrodes were placed in heparinised blood plasma under sterile conditions. Both electrodes were connected to a pH meter. The plasma was bubbled with a special gas mixture (5% $CO_2$ and 20% $O_2$, balance $N_2$) and was constantly stirred. Samples of 1 ml were taken before and 1, 2, 6 and 24 hours after electrode placement. A plasma sample treated identically for 24 hours without an electrode was used as a time control.

3 ml of concentrated nitric acid was added to each 1 ml of plasma sample in a digestion tube and the mixture vortexed. The sample was maintained at room temperature for 30 minutes, then 1 ml of perchloric acid was added. The digestion tube was capped and incubated at 60° C. overnight. The sample was then cooled to room temperature, mixed thoroughly and diluted with 10 ml of de-ionised water.

Samples were analysed using an Inductively Coupled Plasma Mass Spectrometer (ICP-MS, Hewlett-Packard). Briefly, the sample was nebulised with argon gas which carried the finest droplets into the plasma where the sample ionised. Ions were extracted from the plasma into the mass analyser. The mass analyser only allowed ions of a specific mass-charge ratio to pass to the detector at any one time. The detector measured the ion signal at each mass required. Data were expressed as counts per second, which were directly proportional to the concentration of the element at that mass. Antimony was measured at 121 and 123 AMU's. This allowed monitoring of any interference. Interferences in ICP-MS are usually additive, so the lower result was taken. The blank was also measured and subtracted to allow for any contribution from digestion sources. An internal standard was used to compensate for differences between calibration and analytical samples.

Figure 10:
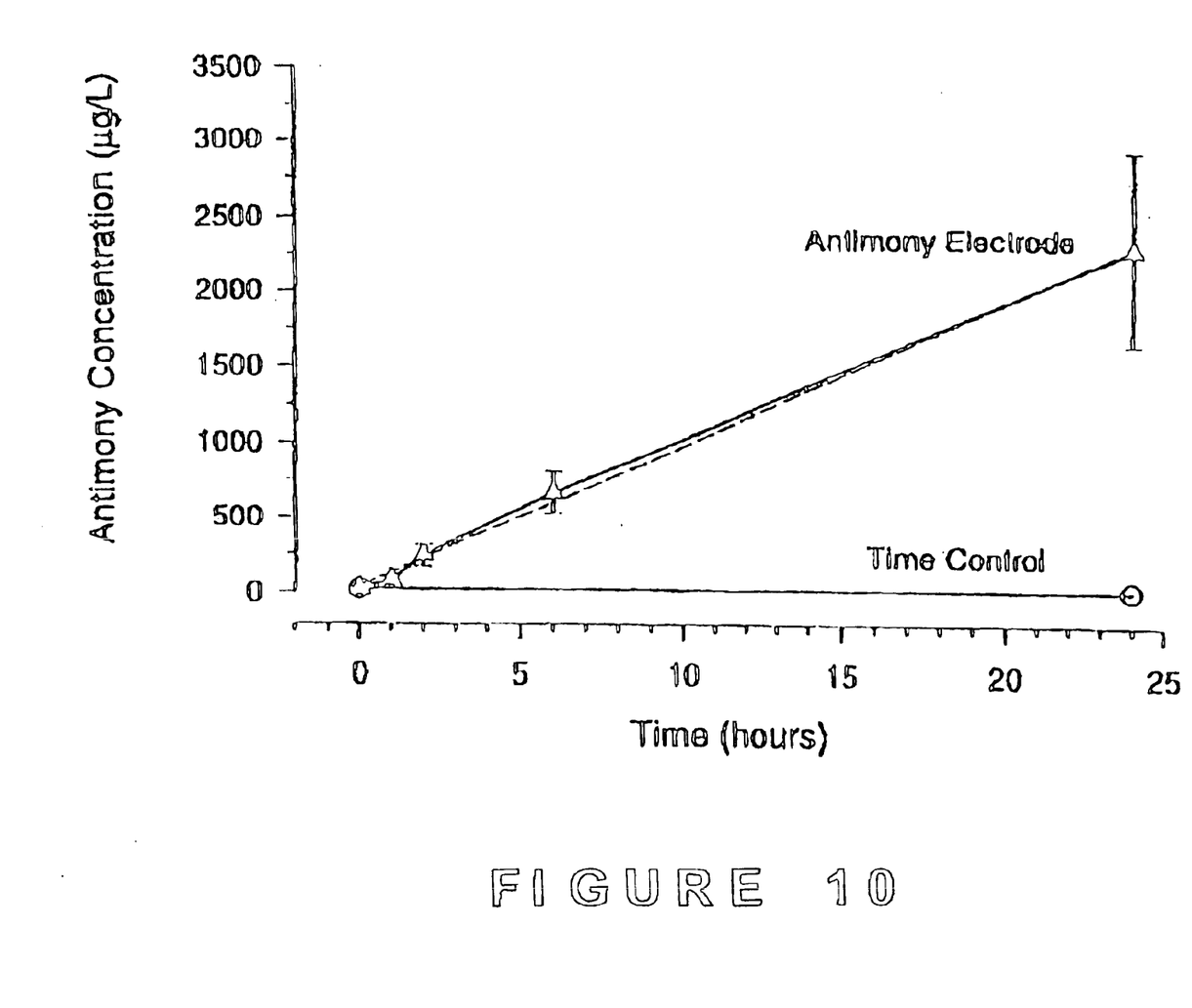
FIG. 10: Change in antimony concentration over time in blood plasma containing an antimony electrode and in blood plasma (time control). The antimony in the pre-insertion and time control samples were just at the limit of detection. After the electrodes were placed, the antimony concentration increased with time at a rate of approximately 94 µg per hour.

The antimony levels in the control samples were close to the detection limit of the ICP-MS measurement. After the electrodes were inserted in the plasma, the antimony concentration showed a linear rise with time at a rate of approximately 94 µg/h ($r^2$=0.997, FIG. 10). The time control was unchanged after 24 hours in comparison with the pre-insertion control value.

pH Measurement by Antimony Electrodes

In the present studies, we showed that antimony electrodes have a slope of −45–52 mV/pH, which is close to the theoretical Nernstian value (−59.16 mV/pH at 25° C.). Slight differences were observed in both slope and intercept at pH 7 between individual electrodes. Such variations indicate the necessity for individual calibration of each electrode.

Although some investigators have reported that antimony electrodes do not exhibit continuous linearity throughout the pH scale, several other studies and our own have confirmed that the response is linear in the physiological range. Differences in the purity of the antimony used and in the fabrication process could contribute to differences in linearity. Antimony electrodes have some advantages over miniature glass electrodes for measurement of tissue pH. A miniature form of antimony electrode can be readily and cheaply produced. The antimony electrode is more physically robust than the miniature glass electrode. The antimony electrode has relatively low resistance and therefore a shorter response time and more stability against external electrical interference than the glass electrode. The antimony electrodes we used in our study were 0.7 mm in diameter. Fibre-optic pH sensors, of similar size to the antimony electrodes used in the present study, have previously been tested and found to cause no obvious injury to the myocardium. The impedance of the antimony electrodes used in the present study was $1-2\times10^5$ ohm. The impedance of a glass electrode is greater than that of an antimony electrode of comparable size by a factor of approximately $10^6$ ohm, which makes for a much greater susceptibility to electrical interference.

Effects of Phosphate Buffers

In our studies, phosphate buffers were used to calibrate the antimony electrodes. Potentially anomalous effects of phosphate buffers on the potential of the antimony electrode have been described by various authors. The effect of phosphate on the mV/pH curve is thought to be due to the formation of antimony complexes. This complex formation has an interfering effect on the mV/pH curve, which is greater in the acidic and neutral ranges. It has been suggested by earlier researchers that phosphate ions less than 0.16 M in the test solution may not interfere. Since a typical phosphate buffer contains 0.1 M phosphate, it would be expected that this interfering effect would be minimal. In our study, 0.1 M phosphate buffers were used. We confirmed the reliability of calibrations using phosphate buffers by comparison with Tris THAM buffer and trimethyl pyridine buffers. These calibrations gave similar results to the ones we obtained with phosphate buffers (data not shown).

Effects of Temperature

We found that antimony electrodes were more sensitive to temperature change than glass electrodes. When temperature increases, the dissociation constant of the water increases and more hydrogen ions are liberated in an aqueous sample medium, so that the solution becomes more acidic. The effect is relatively small in an acidic solution. However, in neutral or basic solutions, the dissociation of water is a significant source of hydrogen ions. Therefore, the pH varies with temperature, especially in a neutral or basic solution. The effect of temperature on the pH of whole blood is estimated by Rosenthal's factor of $-0.0147$ pH/° C. Our measurements with the antimony electrode showed the opposite trend when temperature was varied. The pH observed at warmer conditions appeared higher. The increased pH reading of the antimony electrode at higher temperatures reflects the specific response of the antimony electrode to temperature. A temperature higher than the calibration temperature will yield a more negative potential and result in an alkalosis (pH increase) error. Several investigators have reported temperature responses ranging from 1 to 3 mV/° C., depending on the purity of the antimony used. In our measuring system the reference electrode was separated from the test solution site by a salt bridge. Thus, the temperature of the reference electrode was kept constant, which avoided potential changes in the reference electrode due to temperature change. Although a thermal junction potential develops, due to the temperature difference between one end of the salt bridge and the other, the error introduced is negligible over the range of temperatures from 5–37° C. We observed that the effect of temperature on all the antimony sensors tested was similar. This suggested the possibility of compensation. We therefore developed a computer programme based on the data obtained from our bench work. The measurements after compensation were very close to the true pH confirmed by a glass electrode, either in phosphate buffer solution or blood.

Effect of Oxygen

The effect of $pO_2$ on in vivo pH measurement with antimony electrodes had not previously been well characterised. Our experiments have confirmed and quantified the oxygen sensitivity of the antimony electrode in phosphate buffers and in blood, especially at lower levels of $pO_2$. When the antimony electrode was used to measure the pH of the arterial bloodstream of greyhound dogs, an 0.15 pH unit error occurred. This can be accounted for by the fact that the antimony electrode was calibrated in phosphate buffers in which the $pO_2$ level was about 150 mmHg, whereas the arterial bloodstream had a $pO_2$ level of 220 mmHg. It has been suggested that the manufacturing technique for the antimony probe may contribute to its oxygen or temperature sensitivity. The purity of the antimony used to produce the sensor has been suggested as a causative factor in the oxygen error. However, even use of an ultra-pure antimony electrode (Ventron, 99.8% in purity) results in a decrease in pH with increase in $pO_2$.

It may be argued that, since the antimony electrode potential can be explained by oxygen-dependent corrosion, this potential is inherently oxygen-dependent and thus major interference of oxygen is highly predictable. The corrosion theory excludes the generation of a stable potential by the electrode in an oxygen-free environment. Recently, however it has been shown that the pH response of the electrode remains unchanged in an oxygen-free environment. This suggests that other causes must be invoked to explain electrode function adequately. To assess the suitability of antimony electrodes for measuring myocardial pH, the "true" pH and the gas tension of the tissue under study must be known. For this purpose, we used the Paratrend fibre-optic combined gas and pH sensor. This sensor has been designed for use in the bloodstream. It has also been successfully used for monitoring pH and $pO_2$ changes in tissues such as skeletal muscle and brain. In our experiments, the Paratrend was further validated in the bloodstream by comparison with the results obtained from the blood pH/gas machine. The antimony electrode did respond directionally to the myocardial pH changes produced by infusion of sodium bicarbonate or inhalation of carbon dioxide. However, pH was consistently about 0.4 units higher than measured with the Paratrend (FIG. 9). This difference could be explained by the influence of oxygen. The myocardial oxygen partial pressure obtained with the Paratrend was about 22 mmHg, which is comparable with reported values.

After coronary artery occlusion, myocardial pH (as measured by the Paratrend) dropped by approximately 0.3 pH units in 10 minutes. In contrast, myocardial pH read with the antimony electrodes paradoxically appeared to increase after coronary occlusion. This was undoubtedly due to the influence of oxygen, since the myocardial oxygen level decreased dramatically during coronary artery occlusion. It is clear that the interference of oxygen with the antimony electrode will result in the inaccurate measurement of pH in cardiac surgery, since aortic clamping and cardioplegia produce dramatic changes in myocardial oxygen levels. However, as discussed below ("Conclusions"), it should be possible to compensate for the oxygen sensitivity of the antimony electrode.

Effects of Exposure to Blood

Although we did not test specifically if protein coating affected the performance of the antimony electrode, our pH measurements in protein-free buffer and in blood yielded almost the same readings under controlled conditions of temperature and oxygen. This indicated that deposited protein does not have a significant effect on the antimony electrodes. Other researchers have reported that there was no effect on the pH-voltage response of antimony electrodes when high concentrations of albumin (up to 5.0 g/100 ml) and urea (up to 1 M) were added to phosphate buffers. Thus, we believe that the protein content of blood does not affect the pH reading of an antimony electrode.

Potential Toxicity of Antimony

In clinical use, the toxicity of dissolved antimony from electrodes is of concern. Our polycrystalline antimony sensor was assessed in sterile, heparinised human plasma using techniques simulating clinical use in the arterial bloodstream. Antimony leaching into plasma was determined by use of highly sensitive Inductively Coupled Plasma Mass Spectrometry (ICP-MS). We concluded that the amount of antimony released from electrodes into blood plasma is several orders of magnitude lower than the amount of antimony accepted for administration as a medical therapeutic.

pH probes according to the present invention have been tested for biocompatibility in accordance with ISO standards (ISO 10993). Biocompatibility testing was completed by North American Science Associates (Cincinnati, Ohio, United States of America). Thus, these electrodes are safe, and are comparable to monocrystalline antimony sensors from the toxicological point of view.

Tissue pH Measurement

Other non-invasive methods have been tried to measure myocardial pH. Tissue pH can be derived from the chemical shift of the magnetic resonance spectrum using nuclear magnetic resonance. However, this non-invasive method lacks stability and reproducibility and is cumbersome, since large magnets are required to generate the magnetic field and the whole heart must be placed in the magnetic field.

Use of miniature sensors is the most practical way of measuring intra-myocardial pH. The pH electrode inevitably causes some local tissue damage. Interstitial pH is known to be higher than Intracellular pH by 0.2–0.3 pH units. Placement of a sensor 1.0 mm or more in diameter in the myocardium might injure the cells and cause intracellular release of substantial amounts of hydrogen ion, or cause local ischaemia, resulting in lower pH readings. Therefore, sensors must be in a miniature form. Most miniature sensors have limitations for on-line measurement of pH during cardiac surgery. Ion selective field effect transistors (ISFETS) have been employed In biomedical applications such as gastroenterological pH measurements, but they are not yet small enough for use in cardiac surgery. Fibre-optic colorimetry, as employed in the Paratrend, has been developed for clinical use. A pH-sensitive dye is contained behind a porous membrane in the probe, and colour change information is relayed via fibre-optic cable to a colour analyser. At this stage, this system is only reliable within a narrow pH range. Lack of physical robustness in tissue and high cost are other problems. Currently, glass electrodes represent the most reliable means of clinical measurement of tissue pH. However, problems such as fragility and high impedance have limited their clinical usage, and the antimony electrodes of the present invention represent a significant improvement.

Conclusions

These trials indicate that the basic construction and performance of the antimony electrodes of the present invention make them potentially suitable for in vivo use for measurement of myocardial and oesophageal pH. The response of the antimony electrode to pH alteration is linear in the physiological range. Although the electrodes are sensitive to temperature changes, the temperature error can be eliminated by using temperature compensation, and although oxygen interference is also a difficulty, there are means of compensating for this problem. The pH electrode may be calibrated for the particular oxygen concentration which is present. In a particularly advantageous embodiment, the pH electrode can be combined with a meter for measuring oxygen concentration, thereby providing for automatic calibration of the pH electrode with respect to the oxygen concentration.

An advantage of the antimony electrodes of the present invention is the degree of miniaturisation which is possible. Another major advantage is that they can be sterilised (eg in an autoclave or by gamma radiation) and reused as many as ten times.

In summary, our studies suggest that the improved antimony electrodes of the present invention provide accurate determination of blood, tissue and gastrointestinal pH under conditions of constant oxygen concentration. Temperature compensation can be used to eliminate temperature error. Our experiments do, however, highlight the importance of calibrating the electrode at the same oxygen concentration as can be expected to be experienced in clinical use, or otherwise compensating for the oxygen sensitivity of the electrode.

What is claimed is:

1. A pH electrode having a pH-sensitive region on an electrically conductive support, said pH-sensative region comprising
    a mixture of between 50 and 85% of the total mixture by weight of metal particles, said metal particles consisting of particles of antimony and optionally particles of Group VIII metals, particles of additional Group VA metals other than antimony, or both, and
    a polymer substrate of a non-shrinking polyimide having a resistivity of 10 to 100 Kohms/square;
    wherein the mixture of metal particles is incorporated in, or applied to, the polymer substrate
    and, wherein when said particles are incorporated into said resistive polymer substrate, said pH-sensitive region is abraded to expose said particles.

2. A pH electrode according to claim 1, wherein said metal particles includes particles of platinum, ruthenium or bismuth.

3. A pH electrode according to claim 1 having a pH-sensitive tip or head.

4. A pH electrode according to claim 3, wherein the pH-sensitive head is cone shaped.

5. A pH electrode according to claim 1, wherein the polymer substrate is made partially electrically conductive with carbon and/or silver.

6. A pH electrode according to claim 5, wherein the polymer substrate includes 5 to 25% of carbon black.

7. A pH electrode according to claim 1, wherein the metal particles have a maximum particle size of about 50 microns.

8. A pH electrode according to claim 1, wherein the metal particles are on the outer surface of the polymer substrate.

9. A pH electrode according to claim 8, wherein the pH-sensitive region has a smooth outer surface.

10. A pH electrode according to claim 9, wherein the support is copper wire.

11. A pH electrode according to claim 10, wherein said means is a meter for measuring oxygen concentration.

12. A pH electrode according to claim 1, wherein the pH-sensitive region comprises a mixture of the metal particles incorporated into the polymer substrate.

13. A pH electrode according to claim 1, wherein the support is metallic wire.

14. A pH electrode according to claim 1, further comprising means for calibration of the pH electrode with respect to oxygen concentration.

15. A pH electrode according to claim 1, wherein the pH-sensitive region forms a band extending around a tubular support.

16. A method of measuring the pH of a sample, comprising the steps of contacting a pH electrode according to claim 1 and a reference electrode with the sample and determining the potential difference between the pH electrode and the reference electrode thereby measuring the pH of the sample.

17. The method according to claim 16, wherein the pH of a body fluid, muscle, the gastrointestinal tract or the respiratory tract is measured.

18. The method according to claim 17, wherein the pH of extracellular fluid, blood, lymph, cerebro-spinal fluid, cardiac muscle, skeletal muscle, smooth muscle, the oral cavity, the pharynx, the oesophagus, the stomach, the small intestine, the colon, the biliary tract or the respiratory tract is measured.

19. A method for preparing a pH electrode comprising formation of a pH-sensitive region on an electrically conductive support by applying thereto a polymer substrate of a non-shrinking plastic selected from polyimides, having a resistivity of 10 to 100 Kohms/square, said polymer substrate further comprising between 50 and 85% of the total mixture by weight of metal particles, said metal particles consisting of particles of antimony and optionally particles of Group VIII metals, particles of additional Group VA metals other than antimony, or both incorporated therein or applied thereto either before or after application of said polymer substrate to said support, wherein when said particles are incorporated into said resistive polymer substrate, said pH-sensitive region is abraded to expose said particles.

20. A method according to claim 19, wherein said metal particles include particles of platinum, ruthenium or bismuth.

21. A method according to claim 19, wherein said pH-sensitive region is formed as a tip or head on said support.

22. A method according to claim 21, wherein the pH-sensitive region is formed as a cone-shaped head.

23. A method according to claim 19, wherein the polymer substrate is made partially electrically conductive with carbon and/or silver.

24. A method according to claim 19, wherein the metal particles are applied, by sprinkling, dusting or dipping, to the substrate.

25. A method according to claim 19, wherein the metal particles are incorporated by mixing into the substrate.

26. A method according to claim 25, wherein the pH-sensitive region has a smooth outer surface.

27. A method according to claim 19, wherein the support is metallic wire.

28. A method according to claim 27, wherein the support is copper wire.

29. A method according to claim 19, wherein the pH-sensitive region forms a band extending around a tubular support.

30. A method of measuring the pH of a sample, comprising the steps of contacting a pH electrode prepared by the method of claim 19 and a reference electrode with the sample and determining the potential difference between the pH electrode and the reference electrode thereby measuring the pH of the sample.

* * * * *